(12) United States Patent  
Simpson et al.

(10) Patent No.: US 7,499,165 B2  
(45) Date of Patent: Mar. 3, 2009

(54) SYSTEM OF MEASURING LIGHT TRANSMISSION AND/OR REFLECTION

(75) Inventors: Jeffrey A. Simpson, Wayne, NE (US); Mark A. Imbrock, Sylvania, OH (US); Nathan Strimpel, Carleton, MI (US)

(73) Assignee: Electronic Design To Market, Inc., Toledo, OH (US)

( * ) Notice: Subject to any disclaimer, the term of this patent is extended or adjusted under 35 U.S.C. 154(b) by 0 days.

(21) Appl. No.: 11/375,730

(22) Filed: Mar. 14, 2006

(65) Prior Publication Data

US 2006/0209304 A1 Sep. 21, 2006

Related U.S. Application Data (60) Provisional application No. 60/662,062, filed on Mar. 15, 2005.

(51) Int. Cl.
*G01J 3/50* (2006.01)
*G01N 21/25* (2006.01)
*G01N 21/59* (2006.01)

(52) U.S. Cl. .................. 356/407; 356/420; 356/432; 356/446

(58) Field of Classification Search ................ 356/434, 356/326, 328, 406, 407, 420
See application file for complete search history.

(56) References Cited

U.S. PATENT DOCUMENTS

| | | | |
|---|---|---|---|
| 3,910,701 A | 10/1975 | Henderson et al. | |
| 4,838,697 A * | 6/1989 | Kurandt | 356/406 |
| 5,029,245 A * | 7/1991 | Keranen et al. | 250/205 |
| 5,229,841 A * | 7/1993 | Taranowski et al. | 356/406 |
| 5,257,086 A * | 10/1993 | Fateley et al. | 356/328 |
| 5,303,037 A * | 4/1994 | Taranowski | 356/406 |
| D362,810 S | 10/1995 | Seaburn et al. | |
| 5,477,322 A * | 12/1995 | Webster | 356/328 |
| 5,488,474 A * | 1/1996 | Fateley et al. | 356/326 |
| 5,671,059 A * | 9/1997 | Vincent | 356/402 |
| 6,031,609 A * | 2/2000 | Funk et al. | 356/310 |
| 6,191,860 B1 * | 2/2001 | Klinger et al. | 356/419 |
| 6,373,568 B1 * | 4/2002 | Miller et al. | 356/326 |
| 6,683,695 B1 | 1/2004 | Simpson et al. | |
| 6,690,466 B2 * | 2/2004 | Miller et al. | 356/326 |
| 6,750,964 B2 * | 6/2004 | Levenson et al. | 356/326 |
| 6,859,275 B2 * | 2/2005 | Fateley et al. | 356/330 |
| 6,995,841 B2 * | 2/2006 | Scott et al. | 356/318 |
| 7,126,682 B2 * | 10/2006 | Rowe et al. | 356/310 |
| 7,265,830 B2 * | 9/2007 | Wang | 356/328 |
| 2002/0135763 A1* | 9/2002 | MacKinnon et al. | 356/326 |
| 2004/0218177 A1* | 11/2004 | MacKinnon et al. | 356/326 |
| 2006/0139634 A1* | 6/2006 | Scott et al. | 356/318 |

* cited by examiner

*Primary Examiner*—F. L Evans  
(74) *Attorney, Agent, or Firm*—MacMillan, Sobanski & Todd, LLC (57) ABSTRACT

A system of measuring light transmission and/or reflection has a light transmitter(s) and at least one light sensor which are used to generate a defined light environment over a specified light frequency range.

22 Claims, 7 Drawing Sheets

*Transmission vs. Wavelength of ND-50 and ND-100 Inconel Neutral Density Filters.*

Fig. 5.8 Solar irradiance at sea level.

Figure 13

SYSTEM OF MEASURING LIGHT TRANSMISSION AND/OR REFLECTION

REFERENCE TO RELATED APPLICATIONS

This application claims the benefit of U.S. Provisional Application No. 60/662,062, filed Mar. 15, 2005, the disclosure of which is expressly incorporated herein by reference.

BACKGROUND

Both the automotive industry and law enforcement personnel sometimes encounter problems when vehicles have windows that are coated with films that do not meet state or federal enacted laws. The applied film can change the visible light transmission and reflection characteristics of the entire window assembly. Often, the law enforcement personnel are put at a disadvantage when approaching such vehicle since the personnel cannot readily see into the vehicle.

Currently, there are portable products available on the market which perform at 550 nm and which are used to predict the transmission and reflection performance of the entire visible light spectrum. Such products use a single LED and a single sensor.

In fact, a window film manufacturer might specify the products' entire visible light transmission percentages using this method of prediction. For example, one manufacturer makes dyed films, such as an automotive window film, LLumar® with HPR™ adhesive which specifies the following:

| Type: Non-reflective | AT 35 GN SR HPR |
|---|---|
| % Visible Light Transmission (at 550 nm) | 35 |
| % Total Solar Energy Rejection | 35 |
| % Visible Light Reflection | 7 |
| % Ultra-Violet Light Rejection | 99 |

However, accurate visible light transmission and reflection measurements require that the measurement method be normalized for every wavelength being measured.

The generally accepted measurement range for visible light is 380-720 nm. Law enforcement personnel cannot receive accurate information from a single wavelength or frequency measurement at 550 nm. The light source from such products does not provide energy across the entire visible light spectrum. Further, the light sensor in such products does not have a "flat" or "the same" response for every wavelength across the spectrum. Similarly, there is currently no known single light source available which provides an ideal light spectrum having equal energy at all wavelengths of light from 380-720 nm.

Figure 1:
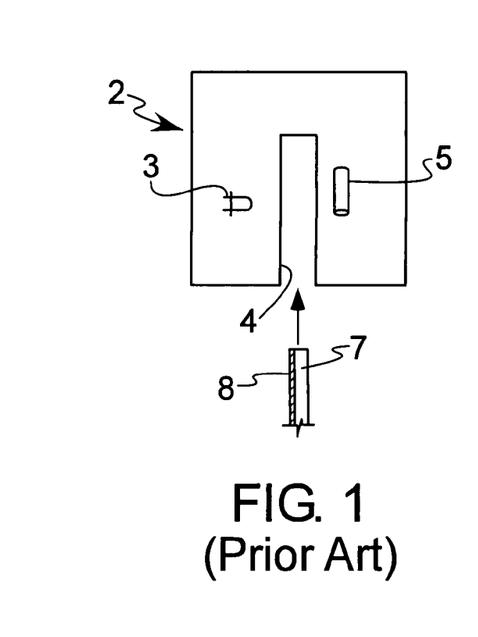

Visible light transmission (VLT) and reflection meters on the market for the automotive industry use the technique described above. In order to use such products, the law enforcement officer slides the product over an edge of the glass. Prior art FIG. 1 schematically illustrates a transmission meter 2 with a single light emitting unit 3 and a single light receiving unit 5, and an opening 4 between the single light emitting unit 3 and the light receiving unit 5 for receiving a window 7 having a film 8 thereon.

Alternatively, the product can include a separate transmitting unit and a separate receiving unit which are placed on opposite sides of the glass. See for example, U.S. Pat. No. Des. 362,810.

Figure 2:
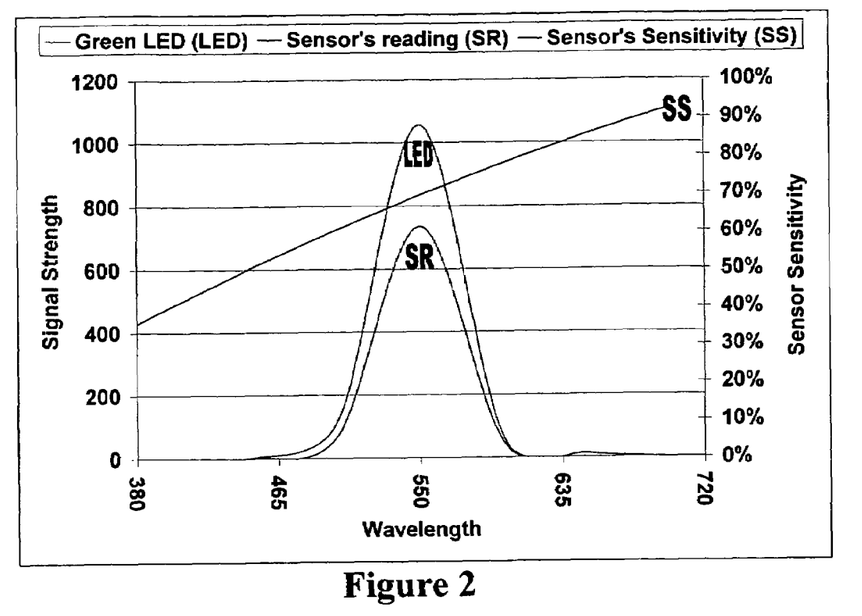
FIG. 2 illustrates the spectrum for a green light emitting diode (LED) at about 550 nm; the photodiode sensor sensitivity (SS) (which is similar to that shown in FIG. 6 herein for 380-720 nm); and, the sensor's reading (SR), or output response, from the non-linear sensor and the limited Green LED spectrum.

These types of products use a single light source and a single light sensor to estimate the entire visible light transmission (VLT) and reflection characteristics of the glass. FIG. 2 illustrates: the spectrum for a green LED at about 550 nm; the photodiode spectral responsivity curve from 380-720 nm (which is similar to that shown in FIG. 6 herein); and, the output response from the non-linear sensor and the limited Green LED spectrum. Thus, the result is not linear and may not accurately measure the transmission since the green LED is only capable of being detected at about the 550 nm range by the receiving unit.

U.S. Pat. No. 3,910,701 uses alternating or sequential LED sources which then are summed together after the measurement is performed.

An alternate form of measuring light transmission is to use a laboratory instrument such as a spectrometer. A spectrometer uses a single broadband light source and characterizes the received light energy into small light frequency ranges of a few nanometers or less. This laboratory instrument analyzes the received light energy on each pixel or element (normally 2048 or greater) on a CCD (charged coupled device) and normalizes the response for each sensing element.

Mathematical manipulation allows the user to select certain light frequency ranges so that individual wavelength measurements can be made on each uniquely defined light sensing pixel or element, and the resulting summation of the data can be made in the laboratory. Thus, the spectrometer uses a prism to separate a broad-spectrum light source into discrete light frequencies that can be mated with individual sensing elements.

SUMMARY

A method for measuring light transmission and/or reflection through a transparent, translucent or semi-opaque medium which includes providing light from multiple transmitters where the transmitted light has desired properties. The desired light properties are sensed with at least one discrete sensor which generates a single output signal over a specified spectral range.

The single output signal substantially directly correlates to the specified wavelength range such as UV, visible, infrared and the like. The single output signal substantially directly correlates to a specified wavelength range in a system property such as one or more of a "flat" environment, a photopic environment, or an environment representing the sun, and the like.

A system for measuring light transmission and/or reflections in one or more transparent, translucent or semi-opaque media includes multiple light transmitters for transmitting light through the medium where the transmitted light has at least one desired property. At least one light sensor senses the desired light property, and generates a single output signal.

In certain embodiments, a proportionate amount of light in each range is used to achieve an end result which represents a specified environment.

BRIEF DESCRIPTION OF THE DRAWINGS

Prior Art FIG. 1 schematically illustrates a light transmission meter.

DETAILED DESCRIPTION

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are described herein.

For ease of explanation, only the explanation of light transmission measurements will be shown and described in detail herein. However, it should be understood that the system integration for a defined light range is the same for both transmission and reflection measurements. In addition, only the explanation of light in the visible light spectrum (approximately 380-720 nm) will be shown and described in detail herein. However, it should be understood that the same type of system integration can be applied to infrared (IR), ultraviolet (UV), and other specified light ranges as well.

The light measuring system significantly improves visible light transmission and reflection measurements. The light measuring system is useful to readily and accurately measure the visible light transmission and/or light reflection of one or more transparent, translucent and semi-opaque media, either alone or in combination. Examples of such measurable media include, for example, but are not limited to one or more of: film such as coated films on glass or plastics; glass such as automobile windows, adjustable darkness glass, user adjustable privacy glass, eyeglass lenses, architectural windows with or without coatings or layers of light-altering materials; plastics such as windows, storage containers; transparent metal layers such as those found in photovoltaic devices and solar panels; polished rocks such as diamonds; liquids such as oils for detecting contaminants therein; gases for detecting smoke or particulates therein; and, air for detecting the overall air quality.

Figure 3A:
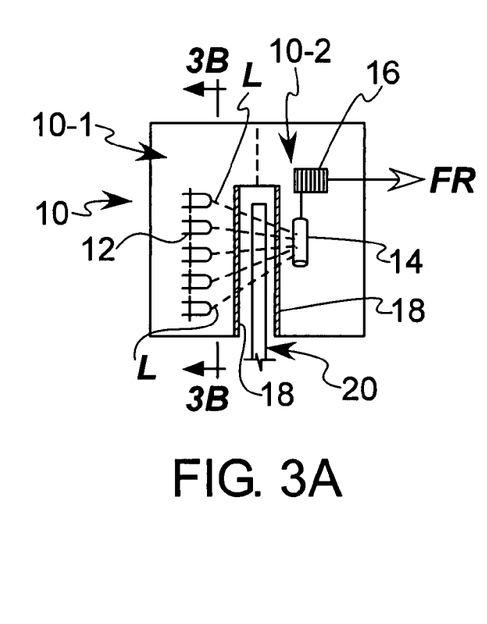
FIG. 3A is a schematic illustration of a light measuring system.

FIG. 3A schematically illustrates a light measuring system 10 having one or more discrete light transmitters 12 and at least one light sensor 14. The light transmitter 12 is combined, or aligned, with the light sensor 14 such that the light, L, being transmitted is received and sensed by the light sensor 14.

The light sensor 14 can be operatively connected to an output signal device 16 which provides a final-result "FR" (also referred to herein below as "final result") as a single output signal, which is further explained herein.

Any suitable non-linear (or linear) light sensor 14, which is capable of detecting wavelengths of light in the visible light range of approximately 380 nm to 720 nm, may be used. In certain embodiments, photodiode arrays such as silicon, germanium and other like diodes are useful as light sensors. Other common types of light sensors, such as, for example, charge coupled devices, CCD, are also suitable.

Also, in certain embodiments, one or more optical altering devices 18, such as filters, beam-splitters, lenses and the like, can be used on the light transmitter 12, the light sensor 14, or both. For example, the optical filters 18 may be used to change the light frequency characteristics of the light transmitter 12 or the non-linear light sensor 14 in the light measuring system. The change in response to the individual light frequency characteristics may allow for easier system matching in order to generate the single output signal from the defined light environment.

Figure 3B:
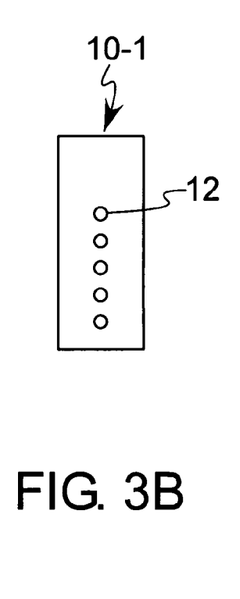
FIG. 3B is a schematic illustration taken along the line 3B-3B in FIG. 3A, showing one configuration of light transmitters.
Figure 3C:
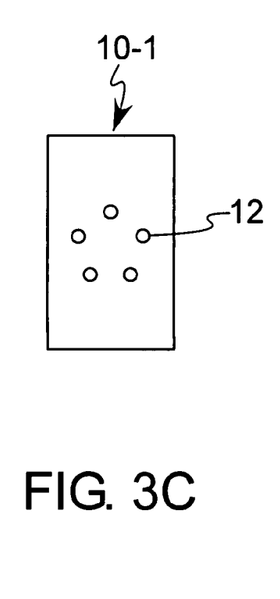
FIG. 3C is a schematic illustration, similar to the view in FIG. 3B, showing another configuration of light transmitters.

FIG. 3B is a schematic illustration taken along the line 3B-3B in FIG. 3A, showing one configuration of light transmitters 12 where the light transmitters 12 are arranged in a substantially linear relationship with respect to each other. FIG. 3C is a schematic illustration, similar to the view in FIG. 3B, showing another configuration of light transmitters 12 where the light transmitters 12 are arranged in a circumferential relationship with respect to each other. It is to be understood that the configuration of the light transmitters 12 can be varied, depending in part, on the desired configuration of the light measuring system 10.

In certain embodiments, the multiple light transmitters 12 substantially simultaneously transmit light to the sensor 14.

There is a specified relationship between the light transmitters 12 and the light sensor 14 such that the output signal has the same response to every wavelength over the visible light spectrum. The light measuring system 10 applies all the light transmitters within the specified spectral range at one time, and not in an alternating or sequential method, so that a total integration of the light measuring system is thus achieved.

The light measuring system 10 generates a single output signal (i.e., flat). The response of the output signal is substantially the same for all light frequencies that pass through the material 20.

The light measuring system 10 uses multiple light transmitters 12 where each light transmitter 12 can have a defined spectral region. For example, in certain embodiments, the light measuring system 10 can have five light transmitters 12, each of which transmits light in a specific spectral range. Also, as shown in FIG. 3, a unitary light measuring system 10 is configured to be removably slid or mounted on, or against, opposite sides of a medium 20 being tested for light transmission or light reflection.

It is to be understood, however, that the light measuring system 10 can be comprised of separate elements, a light transmitter element 10-1 and a light sensor element 10-2, as shown by the dashed line in FIG. 3. The light transmitter element 10-1 and the light sensor element 10-2 are configured to be removably mounted against opposite sides of the medium 20 being tested for measuring light transmission or light reflection of the medium 20. In such embodiments, the light transmitter 12 and the light sensor 14 are housed separately in the light transmitter element 10-1 and the light sensor element 10-2, respectively. The light transmitter element 10-1 and the light sensor element 10-2 can be brought into alignment on opposite sides of the medium 20 so that the light being transmitted from the light transmitter 12 is accurately received by the light sensor 14 and the single output signal is accurately generated.

In certain embodiments, the light transmitters 12 are chosen to generate a specified light interaction over a defined wavelength region. Thus, the light transmitters 12, any optional optical device 18, and the non-linear output signal response of the light sensor 14 are combined and integrated to generate a single output signal for the defined wavelength region.

The light transmitters 12 can generate narrow spectral ranges such that the narrow spectral ranges are combined with non-linear characteristics of the light sensor 14 to generate the single output signal. Alternatively, in another embodiment, the light transmitters 12 can generate broadband spectral ranges that are combined with non-linear characteristics of the light sensor 14 to generate the single output signal.

The light transmitters 12 can be discrete light transmitters that do not have to transmit continuous portions of the visible light spectrum. Nor do the light transmitters 12 have to transmit evenly spaced ranges of the spectrum. Further, the light transmitters 12 do not have to be arranged in a particular configuration. Since only partial ranges of the spectrum need to be measured, the light measuring system 10 can be comprised of few light transmitters 12, and therefore makes efficient use of such light transmitters 12.

In certain embodiments, multiple light transmitters 12 are aligned with one light sensor 14 to generate the single output signal, FR, such that the single output signal represents a specified spectral range.

In certain embodiments, when the final single output signal includes multiple regions of measurement, each measured region provides a proportionate amount of signal as compared to the final combined single output signal. Thus, each measured region is integrated with other measured regions to generate the final-resulting single output signal. The final-result output signal thus represents the specified light environment of the medium being tested.

It is to be noted that while light sensors 14 are understood to have a non-flat (non-linear) spectral response over a range of light frequencies, the light measuring system 10 generates an overall flat spectral response (i.e., the "final-result" single output signal). Thus, the combination of multiple light wavelengths from multiple transmitters 12, the optional optical devices 18, the non-linear light sensors 14, and the defined light frequency ranges (which, preferably, have minimal overlap with other light transmitters) are integrated together to measure a desired light environment and to generate a desired final outcome; the flat-spectral response. However, it is to be understood, that in certain other end-use applications, other light environments can be measured with the light measuring system 10. In such end-use applications, the light transmitters 12 and the light sensor 14 are calibrated, or normalized to the particular light environment. Examples of such end use applications include, but are not limited to, a photopic environment (such as characterization of the human retina, vitreous humor, blood), or a solar-like environment (i.e., imitation of the sun).

In certain embodiments, the light transmitters are adjusted (in conjunction with the sensor) by optical or power output methods to create the specified light environment. Also, in certain embodiments, ambient conditions of the system are measured and the final resulting signal is adjusted to remove the effects of the ambient environment.

Figure 4:
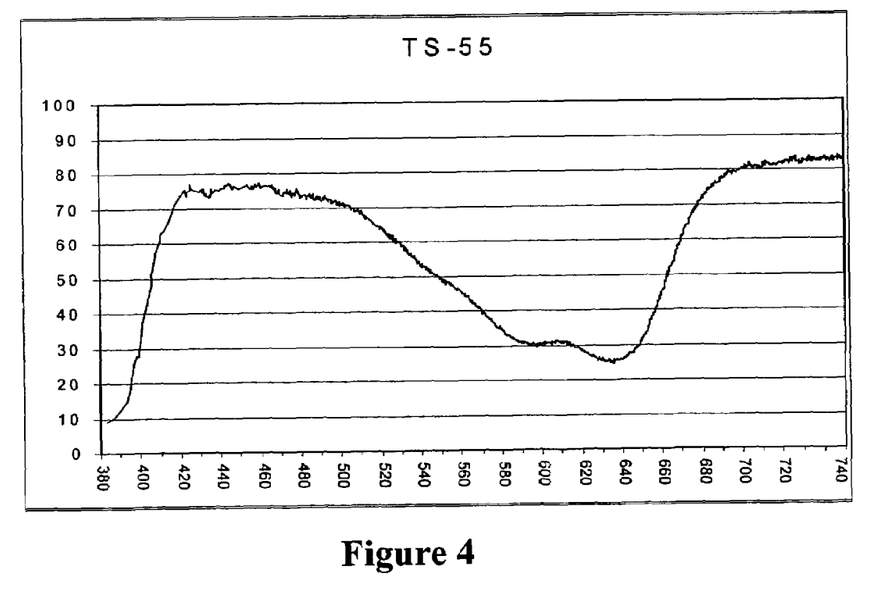
FIG. 4 is a graph of a window film spectrum, showing wavelength in nanometers (X axis), and percent transmission (XMSN) (Y axis).

The need for the light measuring system 10 is shown by light frequency curves of common automotive film. From FIG. 4, it is seen that the response of the film/glass combination is not flat and that using a single 550 nm LED will not generate an accurate response for the entire visible light spectrum.

Figure 5:
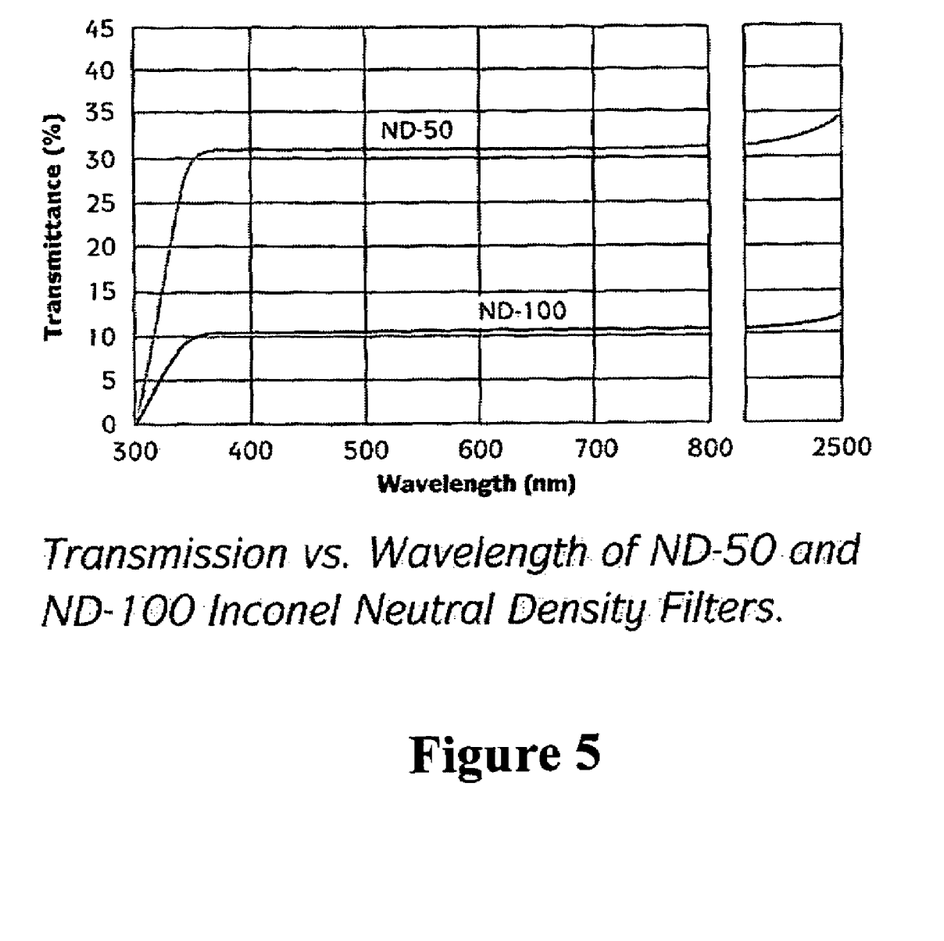
FIG. 5 is a graph showing the transmission versus the wavelength of a Neutral Density (ND-50) filter and a Neutral Density (DN-100) Inconel density filter.

As shown in FIG. 5, a neutral density filter (NDF) has a "flat" spectral response to all wavelengths within a defined range. The neutral density filter will react by the same percent to every wavelength over its allowable range. For example, a 40% neutral density filter will decrease the light energy from a 470 nm or 660 nm LED (or any other light frequency) transmitter the same amount. A defined spectral range with a flat spectral response will react the same to every wavelength just like the neutral density filter.

Figure 6:
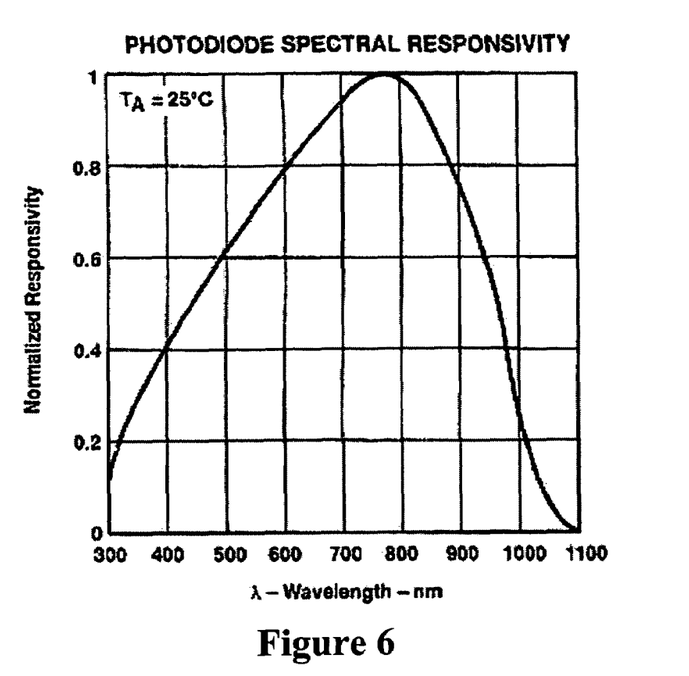
FIG. 6 is a graph of the photodiode spectral responsivity, showing the normalized responsivity versus wavelength.

The visible light region is often specified from 380-720 nm. In certain embodiments, the light measuring system 10 uses a silicon light sensor 14 which, as shown in the photodiode spectral responsivity curve in FIG. 6, is extremely non-linear in its light frequency response. Other types of light sensors may be used; in such embodiments, the light measuring system is then characterized for a flat response.

Figure 7:
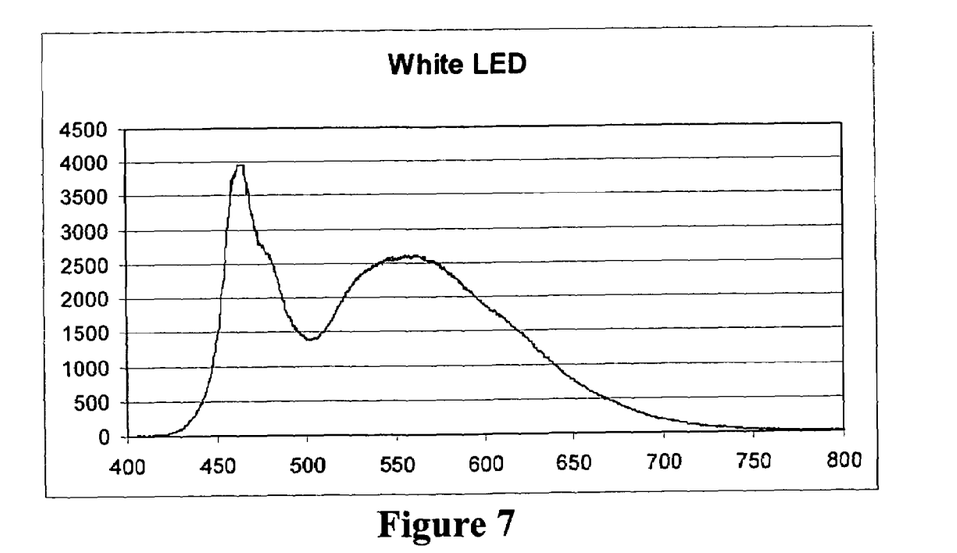
FIG. 7 is a graph showing the spectrum of a white LED.
Figure 8:
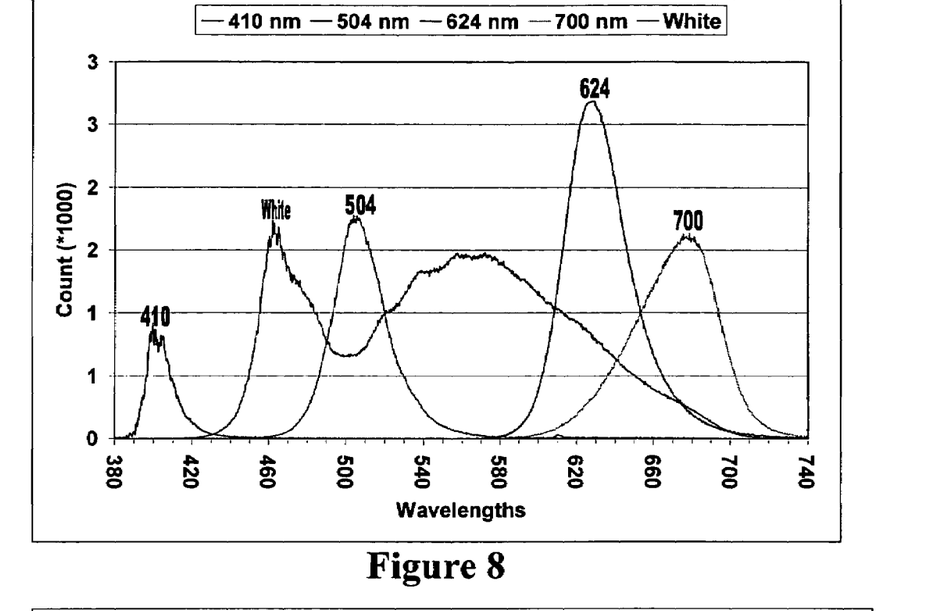
FIG. 8 is a graph showing the spectra of various individual LEDs.

Also, in certain embodiments, LEDs are useful as light transmitters 12 because of the LED's low energy requirements relative to normal tungsten light bulbs. Furthermore, the improvements in LED technology have led to LEDs that now have a broader spectral response. FIG. 7 shows the light response for an exemplary white LED. FIG. 8 shows the white LED spectral response along with the spectral responses of other common LEDs. The use of various types of LEDs allows the light measuring system 10 to combine transmitted light with a non-linear sensor 14 to generate a single output signal, which then represents a specified range for a light frequency environment of the medium being tested. The single output response is substantially "flat"; that is, the same output, or final response, for all wavelengths is generated.

Figure 9:
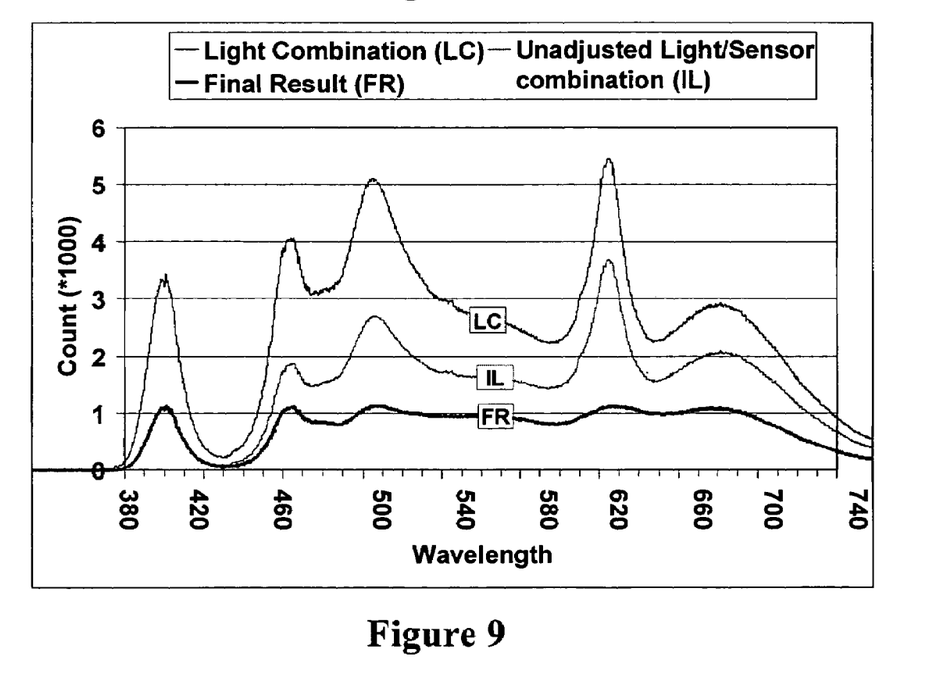
FIG. 9 is a graph showing the spectra for: a combination of LEDs (LC), unadjusted light/sensor combination (IL), and the flat-result (final result) (FR).

The specified light frequency ranges may then be combined together to generate the overall desired spectrum which is received by the non-linear (linear) light sensor. Correlating the ranges to the sensor then generates a generally flat overall system response over a larger specified range. Thus, it is to be noted that even "white" LEDs have a limited range of spectral output; therefore, if a 380-720 nm visible light meter is desired, then other LEDs are needed, as shown in FIG. 8. As such, when multiple light transmitters 12 are combined appropriately with the non-linear light sensor 14, a substantially accurate single output signal for the environment of the medium being tested can be achieved, as shown by the FR "final result" shown in FIG. 9. For explanation purposes, LC is the raw spectral output of the transmitters, IL is the uncorrected spectral response of the sensor to the LC, and FR is the final resulting signal created by additional system adjustments (i.e. filters or output power of transmitter elements).

Also, in certain embodiments, at least one first light transmitter is combined, or aligned, with the sensor to generate a first signal, thus creating a first light environment. A second light transmitter is combined or aligned with the light sensor to generate a second signal, thus creating a second light environment. The first signal is then combined with the second signal to generate the single output signal.

The light measuring system 10 may be normalized by using the output signal response from the sensor 14 to correlate the light transmitters 12 to the appropriate proportion of a combined output signal. Therefore, for example, if multiple ranges are needed for a 380-720 nm visible light measuring system 10, then a 410 nm LED represents approximately 15.8% of the usable range (i.e., 380-434 nm) and its output signal response would be approximately 15.8% of the total signal. If a white LED is used in conjunction with the other LEDs to fill the remaining range from 434-720 nm, the combined output from the LEDs and sensor must be 84.2% of the total signal value. The total combination of multiple specified light ranges would then be 100%. The final output signal result is highly linear across the specified operating range.

Thus, in certain embodiments, each light transmitter is combined with one sensor for a particular spectral range. Each combination forms a subset, and the subsets together provide the proportionate amount of a total specified light range, and thereby generate the single output signal for the overall spectral range.

Each light transmitter 12 is preferably matched to the light sensor 14 for its specified light sensing range. The same may be done with individual light sensors 14 such as red, green and blue (RGB) sensors, which may be used to define spectral ranges. Thus, a RGB system is broken up into 3 ranges. These ranges then use light transmitters in each range to generate a flat spectral response over the range of that sensor and the appropriate percent of the total output is then generated. Each range is then combined using its appropriate percent to achieve the overall desired entire final response.

Figure 10:
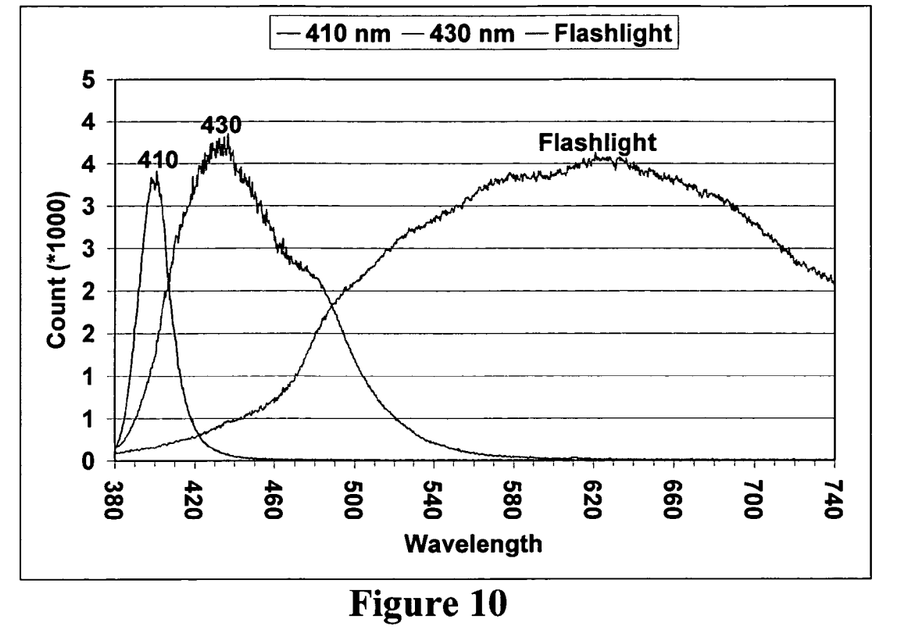
FIG. 10 is a graph showing a flashlight spectrum and two LEDs spectra.
Figure 11:
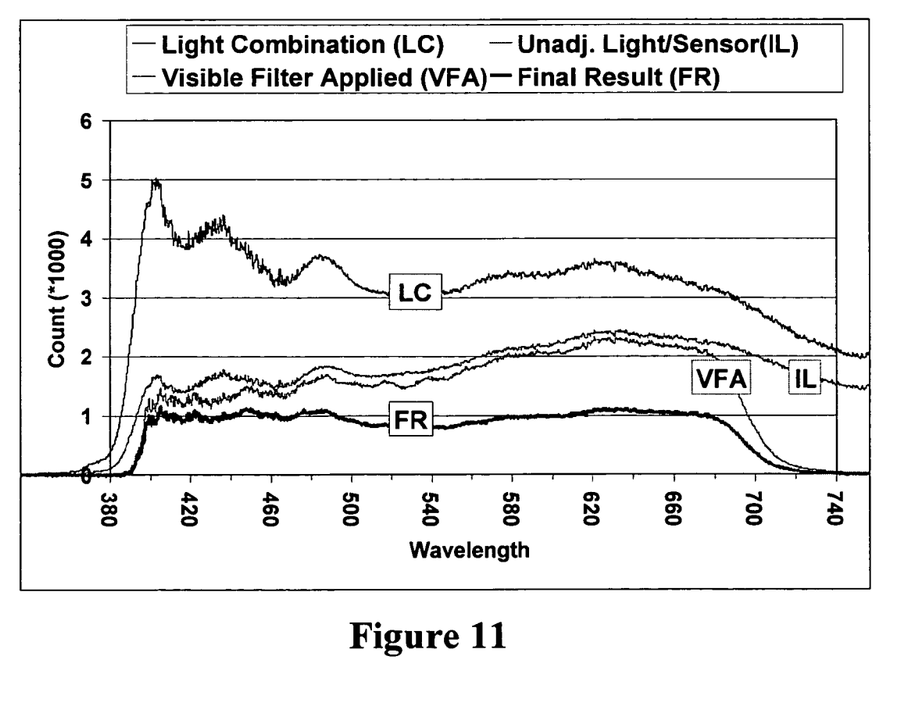
FIG. 11 is a graph showing the spectra for: a light combination (LC), an unadjusted light/sensor combination (IL), a visible light filter (VFA), and a flat-result (final result) (FR).

The spectrum response of a standard tungsten flashlight bulb and 2 LEDs is shown in FIG. 10. Combining a standard flashlight bulb, 2 LEDs, the non-linear nature of the silicon light sensor and a visible light filter, a highly linear result is accomplished, as shown in the "final result" (FR) in FIG. 11. The purpose of the optical filter was to remove the wavelengths from the flashlight bulb that are beyond the visible light region.

In certain end use applications, by providing a small, portable hand held light reflection and transmission measuring system 10 which combines light in this manner, law enforcement personnel and companies which apply film to vehicle glass can easily and accurately determine if a vehicle is in compliance with state and federal laws.

In another end use application, a substantially "flat" spectral response (i.e., single output signal) may also be generated by defined light environments that complement each other to generate a final desired flat spectral response. One example is to generate an environment which may have a positive slope response over the defined light range and a negative response over the same range from another light(s)/transmitter combination, so that the final result would be a "flat" spectral response.

Figure 12:
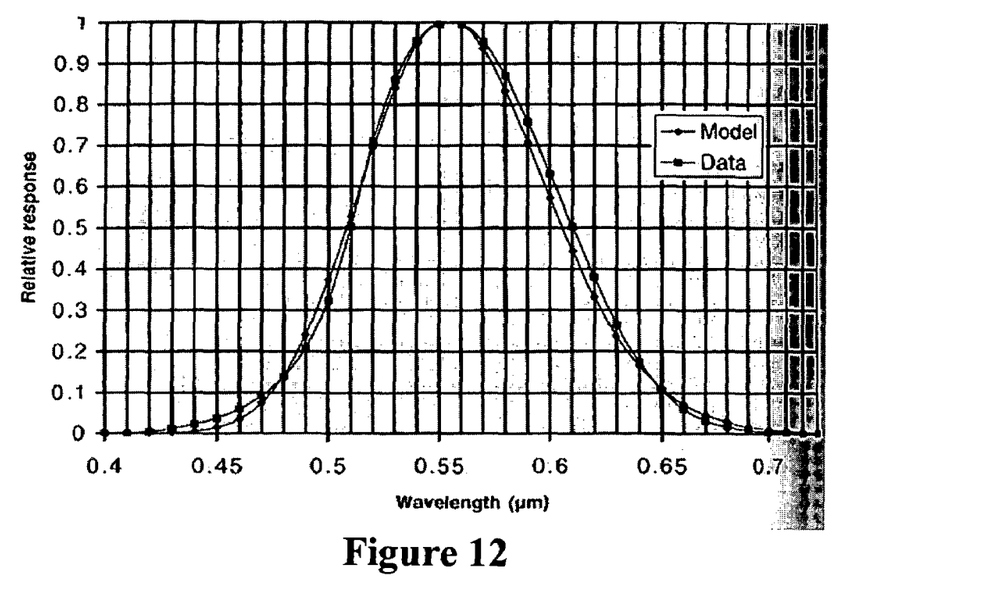
FIG. 12 is a photopic curve showing the spectral response of the human eye.
Figure 13:
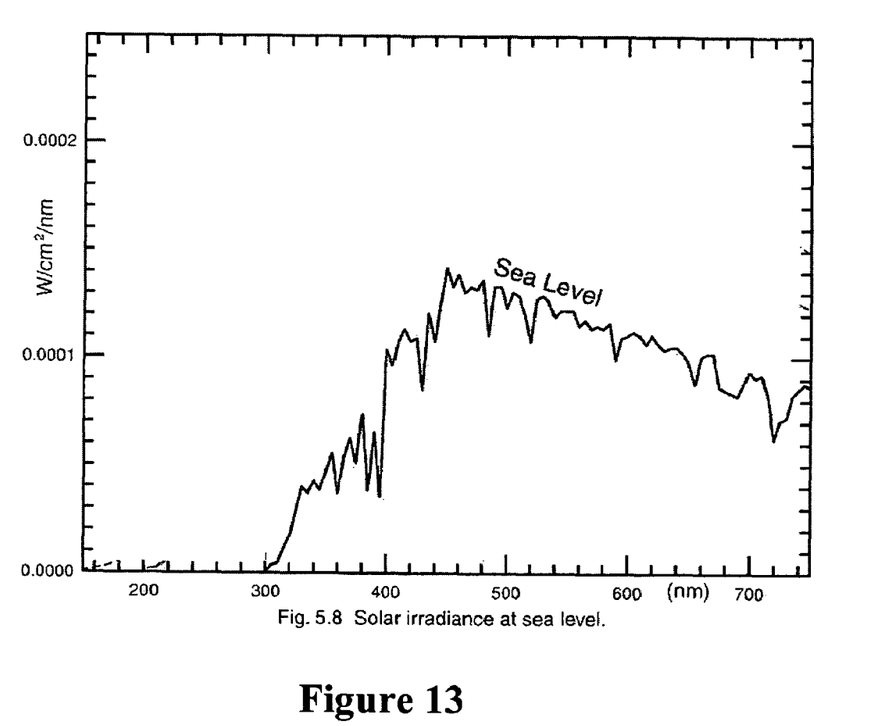
FIG. 13 is a graph showing the solar irradiance of the sun.

Multiple light transmitters may be combined to create multiple lighting environments that can be combined together to represent a specified environment; for example a flat, photopic environment (as shown in FIG. 12), or a solar environment (as shown in FIG. 13).

It is to be understood that various suitable algorithms or mathematical techniques for generating and/or processing the single output signal can be used. Further, the light measuring system may be controlled and/or operated by conventional control and/or operational systems, including, but not limited to various software instructions and/or programs. It is to be understood that such instructions and programs are readily available to, or readily programmable, without undue experimentation from the descriptions as provided herein.

While the invention has been described with reference to a preferred embodiment, it should be understood by those skilled in the art that various changes may be made and equivalents may be substituted for elements thereof without departing from the essential scope of the invention. In addition, many modifications may be made to adapt a particular situation or panel to the teachings of the invention without departing from the essential scope thereof, such as, for example, using UV and Infrared light or any other defined range. Therefore, it is intended that the invention not be limited to the particular embodiment disclosed as the best mode contemplated for carrying out this invention, but that the invention will include all embodiments falling within the scope of the claims.

What is claimed is:

1. A system for measuring light transmission and/or reflections in one or more transparent, translucent or semi-opaque media, comprising:

multiple light transmitters configured to transmit light through the medium, the transmitted light having at least one desired property; and, at least one light sensor configured to sense the desired light property, and configured to generate a single output signal, wherein the light transmitter and the light sensor comprise a single unit which is configured to be removably mounted against opposite sides of the medium.

2. The light measuring system of claim 1, wherein the medium comprises one or more of film, glass, plastic, transparent metal layers, polished rocks, liquids, gases, or air, either alone or in combination.

3. The light measuring system of claim 1, wherein the light transmitters are adjusted in conjunction with the sensor by optical or power output methods to create the specified light environment.

4. The light measuring system of claim 1, wherein ambient conditions of the system are measured and the final resulting signal is adjusted to remove the effects thereof.

5. The light measuring system of claim 1, wherein the light environment is divided into multiple spectral ranges.

6. The light measuring system of claim 5, wherein a proportionate amount of light in each spectral range is used to achieve the single output signal.

7. The light measuring system of claim 1, comprising multiple lights transmitters configured to substantially simultaneously transmit light.

8. The light measuring system of claim 1, further including one or more optical altering devices configured to change performance characteristics of the light sensor, the light transmitter, or both.

9. The light measuring system of claim 1, wherein the light transmitters are configured to generate narrow spectral ranges.

10. The light measuring system of claim 1, wherein the light transmitters are configured to generate broadband spectral ranges.

11. The light measuring system of claim 1, comprising multiple light transmitters and one light sensor.

12. A system for measuring light transmission and/or reflections in one or more transparent, translucent or semi-opaque media, comprising:

multiple light transmitters configured to transmit light through the medium, the transmitted light having at least one desired property; and, at least one light sensor configured to sense the desired light property, and configured to generate a single output signal, wherein the light transmitter and the light sensor comprise separate elements which are configured to be removably mounted against opposite sides of the medium.

13. The light measuring system of claim 12, wherein the light environment is divided into multiple spectral ranges.

14. The light measuring system of claim 13, wherein a proportionate amount of light in each spectral range is used to achieve the single output signal.

15. The light measuring system of claim 12, comprising multiple lights transmitters configured to substantially simultaneously transmit light.

16. The light measuring system of claim 12, further including one or more optical altering devices configured to change performance characteristics of the light sensor, the light transmitter, or both.

17. The light measuring system of claim 12, wherein the light transmitters are configured to generate narrow spectral ranges.

18. The light measuring system of claim 12, wherein the light transmitters are configured to generate broadband spectral ranges.

19. The light measuring system of claim 12, comprising multiple light transmitters and one light sensor.

20. The light measuring system of claim 12, wherein the medium comprises one or more of film, glass, plastic, transparent metal layers, polished rocks, liquids, gases, or air, either alone or in combination.

21. The light measuring system of claim 12, wherein the light transmitters are adjusted in conjunction with the sensor by optical or power output methods to create the specified light environment.

22. The light measuring system of claim 12, wherein ambient conditions of the system are measured and the final resulting signal is adjusted to remove the effects thereof.

* * * * *